(12) United States Patent
Pilvisto

(10) Patent No.: US 6,887,195 B1
(45) Date of Patent: *May 3, 2005

(54) ENDOSCOPE-TYPE DEVICE, ESPECIALLY FOR EMERGENCY INTUBATION

(75) Inventor: Tönis Pilvisto, Tallinn (EE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/030,499

(22) PCT Filed: Jul. 7, 2000

(86) PCT No.: PCT/DE00/02223

§ 371 (c)(1),
(2), (4) Date: Mar. 25, 2002

(87) PCT Pub. No.: WO01/03760

PCT Pub. Date: Jan. 18, 2001

(30) Foreign Application Priority Data

Jul. 9, 1999 (DE) ............................. 199 32 022

(51) Int. Cl.⁷ .............................................. A61B 1/00
(52) U.S. Cl. ..................................... 600/146; 600/141
(58) Field of Search ................................ 600/120, 139, 600/141, 146, 147, 148, 149, 150; 604/95.01, 604/95.04

(56) References Cited

U.S. PATENT DOCUMENTS

| | | | |
|---|---|---|---|
| 3,557,780 A * | 1/1971 | Sato | 600/141 |
| 3,998,216 A | 12/1976 | Hosono | |
| 4,529,400 A | 7/1985 | Scholten | |
| 5,179,935 A * | 1/1993 | Miyagi | 600/142 |
| 5,531,686 A | 7/1996 | Lundquist et al. | |
| 5,549,542 A | 8/1996 | Kovalcheck | |
| 5,575,755 A * | 11/1996 | Krauter et al. | 600/148 |
| 5,752,912 A * | 5/1998 | Takahashi et al. | 600/149 |
| 5,762,067 A * | 6/1998 | Dunham et al. | 600/462 |
| 5,842,973 A | 12/1998 | Bullard | |
| 6,033,378 A * | 3/2000 | Lundquist et al. | 604/95.01 |
| 6,699,182 B2 * | 3/2004 | Pilvisto | 600/146 |

FOREIGN PATENT DOCUMENTS

EP 0 301 288 A 2/1989

* cited by examiner

*Primary Examiner*—Beverly M. Flanagan
(74) *Attorney, Agent, or Firm*—The Culbertson Group, P.C.

(57) ABSTRACT

The invention relates to an endoscope-type device, particularly an endoscope for emergency intubation, comprising a holding portion (7) and a shaft (1) which is configured to be flexible at least in partial areas, with at least two longitudinal bendable pulling and/or pushing elements acting on said shaft (1) in the axial direction at different distances from the proximal end, with said pulling and/or pushing elements extending as far as the proximal end and being lockably received in a fixing device.

18 Claims, 4 Drawing Sheets

ENDOSCOPE-TYPE DEVICE, ESPECIALLY FOR EMERGENCY INTUBATION

TECHNICAL FIELD OF THE INVENTION

The invention relates to an endoscope-type device having a shaft that may be manually shaped and then reasonably fixed in the desired shape.

BACKGROUND

Endoscope-type devices are used in many different fields of application, such as medicine, for example endoscopy, particularly for emergency intubation, but also in engineering, for example as endoscope-type tools with an endoscope-type, flexible and formable shaft, and in general fields of application such as the controlled movement of extremities, particularly human extremities.

Intubation is the introduction of a tube (or a catheter) consisting of rubber or plastic material into the larynx and then into the trachea of the individual. It serves to maintain an effective exchange of gases, which is essential for providing organs with oxygen, among other things, and which is usually effected by respiration. In situations in which the patient is not capable of breathing himself any more as a result of an illness, an injury or medication, for example when a narcosis is carried out, artificial respiration has to be carried out. A prerequisite for this artificial respiration is a secure connection between the respirator and the patient's respiratory tract. In order to ensure that air is supplied to the respiratory organs only, without any air reaching the digestive tract via the esophagus, the tube is pushed with its distal end into the trachea via the mouth or the nose and is positioned there in such a way that both lobes of the lung are aerated. At the proximal end, the tube is connected with the tube system of the respirator via a standardized projection (connector).

If the tip of the tube is not positioned in the trachea, the lobes of the lung are not aerated. In this case, the blood flowing through the lung is not enriched with oxygen to a sufficient extent, and the organs are not provided with oxygen any more. Depending on how long the organs are not supplied with oxygen to a sufficient extent, apart from the complete restoration of all bodily functions, permanent cerebral injuries (such as a coma) or even death because of cardiac arrest might be possible. Faulty intubation, meaning those maneuvers of intubation in which the tube is not positioned correctly and the tip of the tube rests in the esophagus instead of the trachea, for example, will have the same consequences.

There are several methods and shapes of tubes to ensure secure positioning of the tip of the tube. With patients for whom no special anatomic or pathological conditions are to be taken into account, intubation is usually easy and fast to carry out with the usual methods, mainly the laryngoscopical intubation. However, difficulties may arise if there are pathological changes or anatomic peculiarities; in this case, the patient, who is not breathing any more, is subjected to artificial respiration by applying a combination of laryngoscopical intubation and fiber-optical intubation or by using devices employed specifically for this purpose.

In emergency intubation, which usually means the intubation of a person who has become unconscious and whose lung is liable to fill with water, it is necessary to supply air from outside as soon as possible in order to minimize the risk of lung injury.

In an emergency situation, i.e. at the site of the accident and usually not in a hospital, this is done by means of laryngoscopical intubation; here, using a laryngoscope, lifting the tongue root and the epiglottis, the patient's pharynx is opened in order to gain a good view on the entrance to the larynx, the rima glottidis. If the rima glottidis is only partially visible, it is difficult to introduce the tube. One manages by changing the shape of the tube in its longitudinal axis until the tip of the tube can securely reach the entrance to the trachea. By now, this has been done by internally splinting the tube by means of a guide rod in the form of a flexible wire sheathed with plastic material which is inserted therein, which is so stable after bending that it transfers its shape in the longitudinal axis to the elastic tube. It is displaceable in the longitudinal axis within the tube, so it may also project from the distal tube end with its soft tip. Depending on the anatomic conditions, the guide rod is bent in such a way that its tip can be pushed through the rima glottidis and the tip of the tube can then be positioned in the trachea by sliding it over the guide rod. If the rima glottidis is not visible because of anatomic difficulties, so the path of the tube or the guide rod cannot be watched when it is pushed forward, there is a higher risk of injuries and a markedly reduced hitting accuracy. Although there are special instruments which are to make it possible to see the rima glottidis even under difficult conditions, the view through the tube is often obstructed when they are used because of the narrow conditions. For this reason, in difficult cases, the application of laryngoscopical intubation is not favorable.

Therefore, in these cases, fiber-optical intubation is preferably applied, in which an endoscope of the type mentioned at the beginning is used in order to find the entrance to the trachea and to illuminate and make visible the area to be inspected. Furthermore, by means of a mechanism mounted on the holding portion of the endoscope, the position of the tip of the endoscope can be changed, and it can therefore be visibly pushed through the rima glottidis. The tube previously placed upon the tube of the endoscope is then pushed forward as far as into the trachea; then, the endoscope is pulled out of the tube which has been positioned correctly, and the tube is fixed to the patient's head and is connected with the respirator.

However, the fiber-optical method cannot be carried out optimally in all cases, either. It is particularly different if the patient is lying on his back and his musculature is slackened, because the tongue root falls back, thus blocking the path to the trachea. Furthermore, as one hand is required to guide the endoscope—usually by means of the surrounding tube—in fiber-optical intubation and a second hand is required to operate the mechanism of the endoscope, another person is necessary to lift the tongue root by means of a laryngoscope; however, such a person is not necessarily present in case of an emergency.

In the document EP 0 742 026 A, a flexible and simultaneously formable endoscope with a viewing lens was therefore suggested, over which a tube can be slid. Here, formability and flexibility was to be obtained by an articulated rod whose individual adjacent links with convex or concave surfaces could be tensed by tensional or compressive forces. What was disadvantageous, however, was that tests during manufacturing revealed that this principle is very complex because of the frictional forces which are difficult to control and that sufficient flexibility with simultaneously adjustable stiffness cannot be realized with this endoscope.

SUMMARY OF THE INVENTION

Thus, the object of the invention is to provide an endoscope-type device at low cost and in a simple manner, which overcomes the above-mentioned drawbacks and which comprises, at least partially, a formable and stiff shaft which, after releasing, changes into a flexible condition at least in these partial areas.

According to the invention, this object is achieved with an endoscope-type device with a fixing device at its proximal end. By arranging longitudinal bendable pulling and/or pushing elements or their distal ends at the shaft at different distances from the proximal end, the shaft can manually be brought into a desired shape in the flexible, i.e. non-fixed condition, which becomes stiff by locking the pulling and/or pushing elements with the fixing device. Here, the pulling and/or pushing elements, which are limited at least in the pushing or pulling direction, act on the shaft, and the stability of the stiffness can be increased by a bilateral limitation.

In an embodiment of the invention, the pulling and/or pushing elements, for example steel strands, may be movably received in guide elements at the shaft in the longitudinal direction. Hereby, the stability of the rigidity is advantageously increased, as the path length of the pulling and/or pushing elements is defined exactly by the fact that the guide elements receiving the pulling and/or pushing elements are fixedly positioned.

In a further embodiment of the invention, seen from a cross-sectional view, the pulling and/or pushing elements are positioned in a ring-shaped arrangement within said shaft (1) at the inner periphery thereof, so their lever action and thus the stability of the rigidity, which increases with increasing distance from the center line, is advantageously improved.

In a further embodiment of the invention, lateral guide means are arranged inside the shaft which, seen in a cross-sectional view, are opposed to each other, and which are fixedly connected with the shaft at least in partial areas. Advantageously, this will prevent undesired bending of the shaft within the plane defined by lateral guide means.

In a further embodiment of the invention, the channel is configured as a channel for an optical light guide and an optical image guide or as a channel for instruments. Advantageously, this makes it possible to check and facilitate the arrival at an aiming point when the endoscope-type device is introduced into a non-visible portion.

In a further embodiment of the invention, pulling and/or pushing elements act on the shaft in pairs in the axial direction, substantially at equal distances from the proximal end. Hereby, as a result of the cooperation of pulling and pushing forces of a pair, stability may be increased. Such pairs of pulling and/or pushing elements may be arranged point-symmetrically at the shaft in order to advantageously exert the optimum stability in a freely movable shaft without any lateral limitation with their maximum distance from each other.

In case of lateral limitation to the movement, however, it may also be advantageous for an optimum effect of the forces to arrange pairs of pulling and/or pushing elements at the shaft to be symmetrical to the horizontal or the vertical axis, in other words: symmetrical to the plane defined by the lateral guide means, respectively.

BRIEF DESCRIPTION OF THE DRAWINGS

In the following, the invention is explained in greater detail with the aid of an embodiment shown in the drawings, in which.

DESCRIPTION OF PREFERRED EMBODIMENTS

Figure 1:
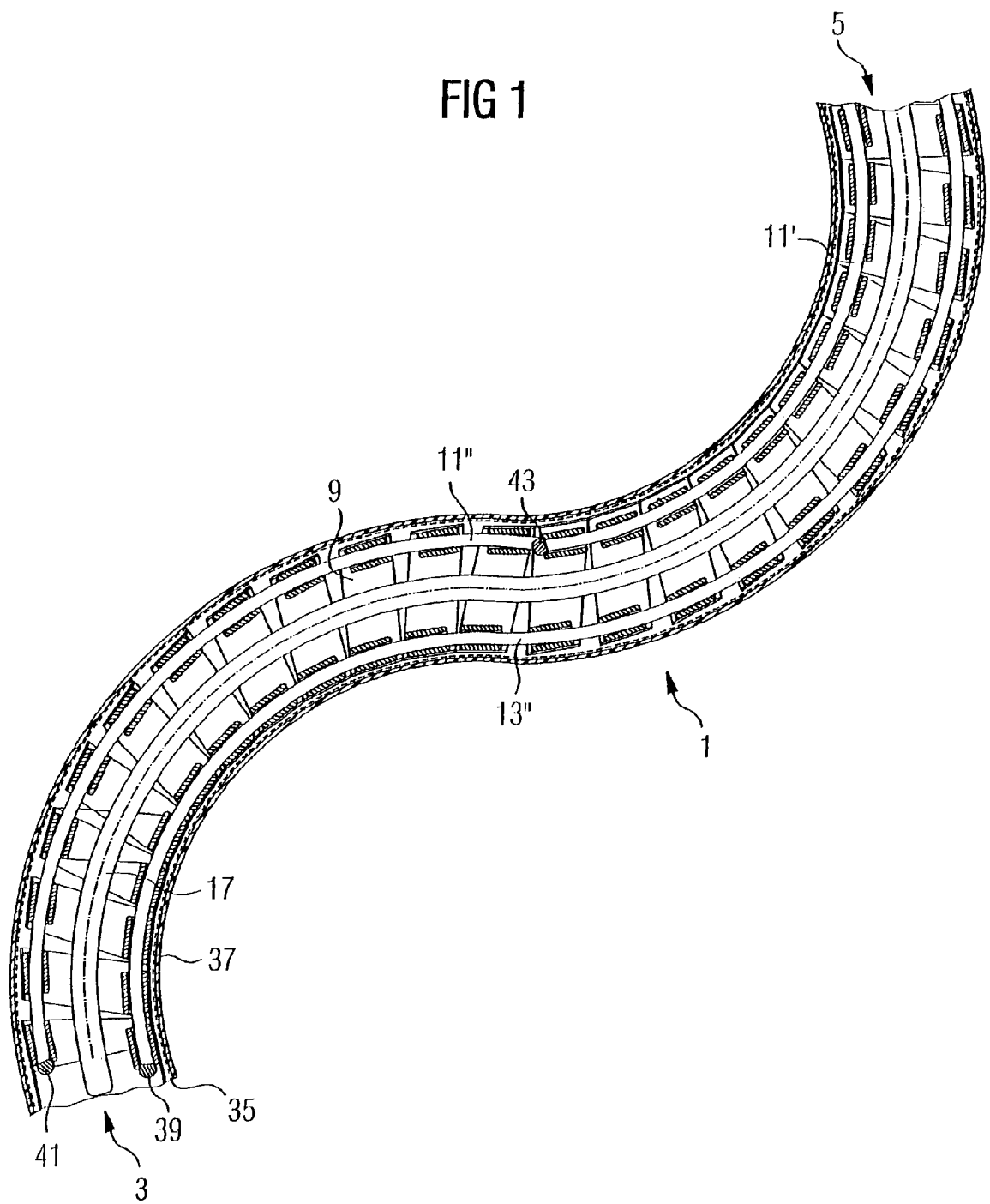
FIG. 1 shows a longitudinal sectional view of a shaft of an endoscope-type device according to the invention.
Figure 4:
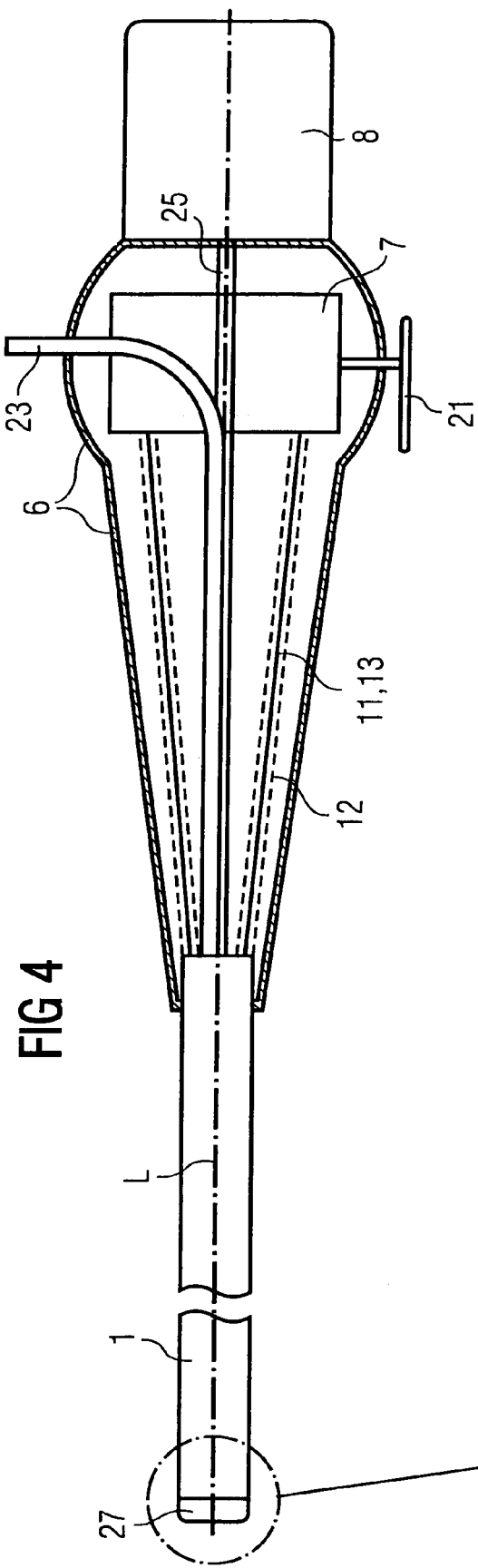
FIG. 4 shows a lateral view in partial section of the endoscope-type device according to the invention.

FIG. 1 shows a shaft 1 of an endoscope-type device according to the invention with a distal end 3 and a proximal end 5. Adjacent the proximal end 5 of the shaft 1, a housing 6 with a holding portion 7 (see FIG. 4) and an eyepiece 8 as shown in FIG. 4 is arranged.

Figure 3:
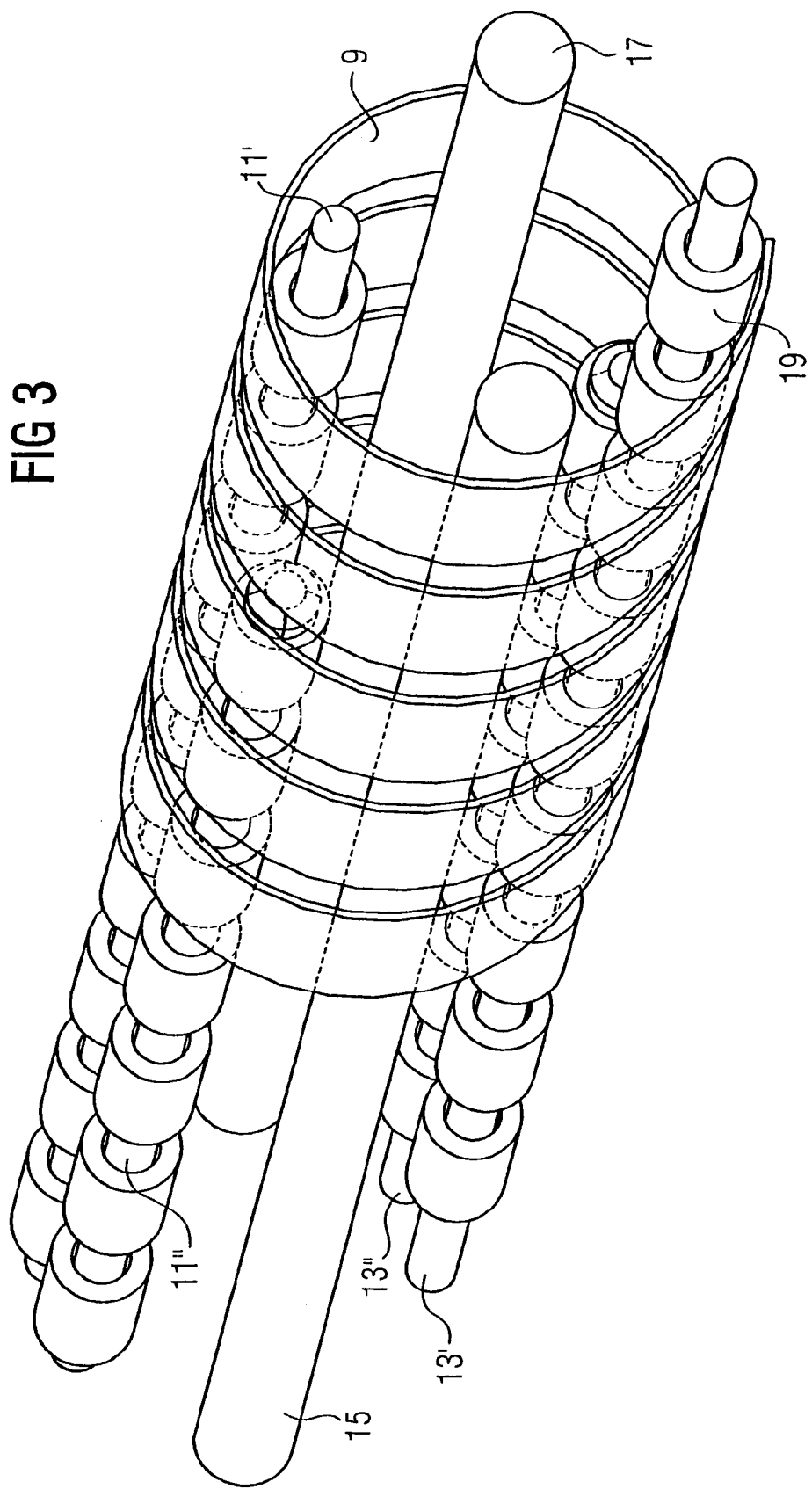
FIG. 3 shows a perspective, schematic view of the structure of a partial portion of the shaft according to FIG. 1.

As will be apparent from FIG. 3, the shaft 1 consists of a spring with a ring-shaped cross-section, particularly a leaf spring 9, which extends from the proximal end 5 to the distal end 3 of the shaft 1. The spring, the ring-shaped cross-section of which includes both the circular shape, the oval shape and the polygonal shape, is made of steel or plastic material, for example.

At the inner periphery or the inner wall of the leaf spring 9, several—for example five— ropes 11 to 11"" guided on top and five ropes 13 to 13"" guided at the bottom and lateral guide means at the left side 15 and the right side 17 are arranged.

Figure 2:
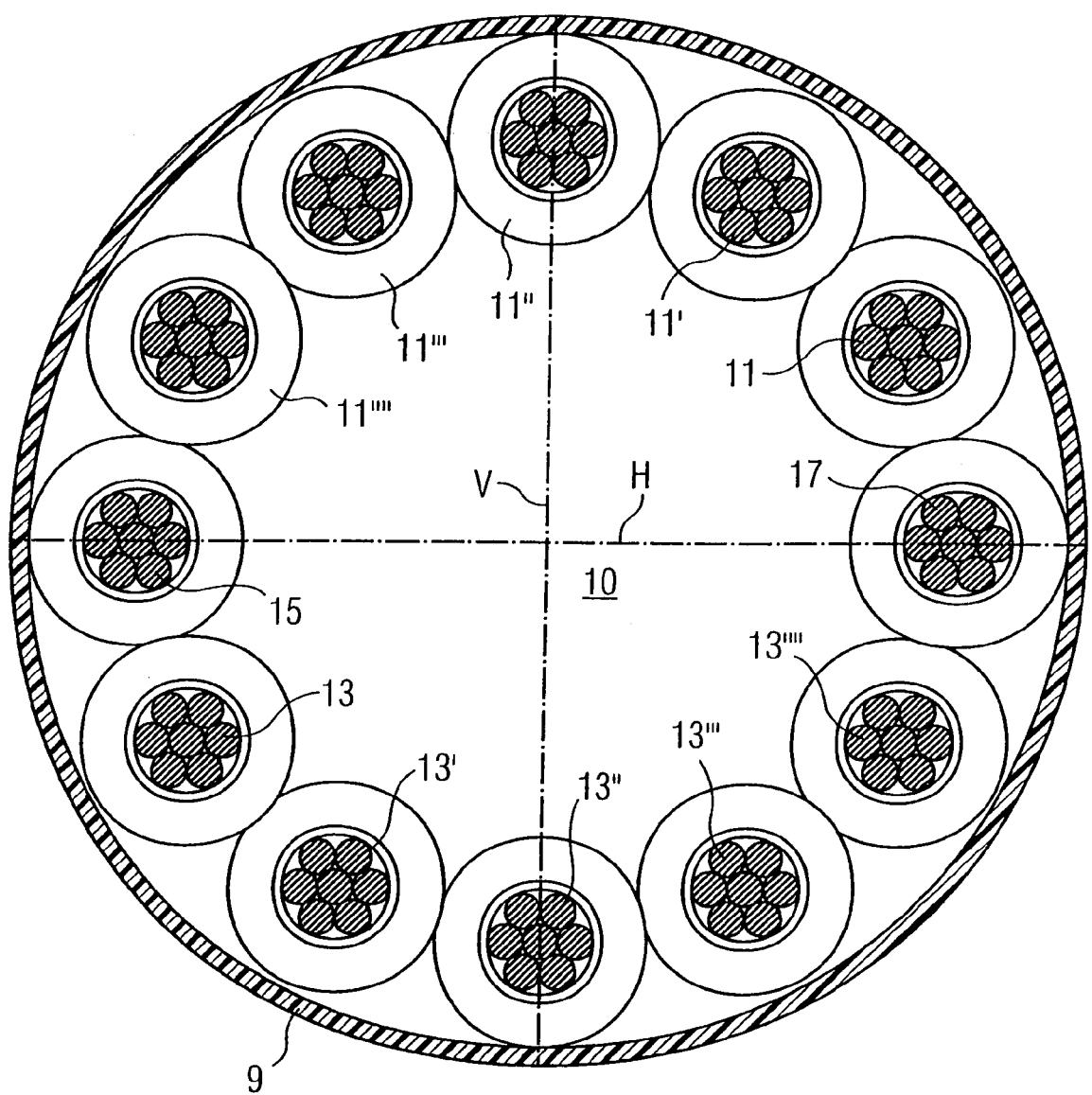
FIG. 2 shows a cross-sectional view of the shaft according to FIG. 1.

The cross-sectional distribution of ropes 11 to 11"", 13 to 13"", 15 and 17 shown in FIG. 2 illustrates that the lateral guide means are positioned, when seen from a cross-sectional view, at the inner periphery of the leaf spring 9 in such a way that they lie opposite to each other in a horizontal mid-plane or are arranged on a horizontal center line H. Above and below the axis H, ropes 11 to 11"" and 13 to 13"" guided on top and at the bottom are arranged at the inner periphery, particularly at equal distances.

As will be apparent from FIG. 2, all ropes may be configured as strands, particularly made of steel or plastic material, with five leads, for example. The ropes 11 to 11"" and 13 to 13"" guided on top and at the bottom extend in guide elements 19 which may be configured to be ring-shaped and which are arranged at the inner periphery in the longitudinal direction and along a longitudinal axis in distances, particularly equal distances, corresponding to the turn or the convolution and the width of the leaf spring, for example by laser welding.

The ropes 11 to 11"" and 13 to 13"", whose outer periphery is of somewhat smaller dimension than the inner periphery of the guide elements 19, are guided out of the proximal end 5 of the shaft in a first conically widened portion of the housing 6 shown in FIG. 4 and extend as far as into the holding portion 7 arranged in the adjacent widened and conical portion. The diameter of the—seen from a cross-sectional view—ring-shaped arrangement of the guided ropes 11 to 11"" and 13 to 13"" increases from some millimeters, such as 3 mm in the area of the shaft (provided that the shaft 1 has an outer diameter of approximately 5 to 6 mm) to approximately the double value. In this area, the ropes 11 to 11'''' and 13 to 13'''' may extend within guide means, too—such as rigid guide means 12 shown in dotted lines in the drawing—in spite of the fact that the holding portion 7 is fixedly arranged in the housing 6, so as not to exert pulling forces only, but also pushing forces.

In its first portion adjacent the proximal end 5 of the shaft 1, the housing 6 is widened correspondingly and is configured to be conical, for example. Next to this first portion, the housing 6 continues to form a widened spherical portion with the holding portion 7. In the first portion, the guided ropes 11 to 11'''' and 13 to 13'''' are guided in a rigid sleeve which is fixedly arranged in the housing.

In this holding portion 7, a fixing mechanism is located which is not shown in greater detail in the drawings and which can be operated by an operating element, such as an operating lever 21, in order to release the proximal ends of the ropes 11 and 13 so as to be movable in their longitudinal direction or to fix them. A fixing device of this kind may be configured as a guide plate arranged perpendicularly to the plane of the drawings, which contains holes with the corresponding geometry, e.g. circular, in one line or in two parallel rows in order to receive the ropes 11 to 13 so as to be movable in the longitudinal direction. Of course, the holes in the guide plate have a slightly larger inner diameter than the outer diameter of the ropes 11 to 11''''and 13 to 13''''. In order to block or release the ropes in their longitudinal direction, a second guide plate which is configured to correspond to the first guide plate and is arranged adjacent to it, and whose holes are aligned in the releasing position, can be displaced with respect to the first plate via the operating lever 21, for example. In this case, the rope ends are clamped in their respective longitudinal position. Thus, the operating lever 21 and the second guide plate, which acts as a clamping plate and can be displaced with respect to the first plate parallel thereto, provide a releasing and a locking position; in these positions, the operating lever and thus the clamping plate can be fixed via locking means or can be pre-stressed permanently in a position, particularly the fixing position, by means of a spring, for example, so as to be put into the releasing position only during the operation of the operating lever. At least in the portion in which they are capable of being displaced in the longitudinal direction inside the fixing device, the rope ends may be configured as rods or may be surrounded by rigid sleeves. Advantageously, this contributes to prevent deterioration or wear, such as splicing of the ends as a result of continued use.

As will be apparent from FIG. 4, in the area of the partially spherical section which is located adjacent the conical first section of the housing and which includes the holding element 7, an optical light guide is guided from inside the housing to the outside so as to be connected to a light source which is not shown in the drawings. The cylindrical portion, which forms the proximal end of the housing and which has a smaller diameter than the spherical section, is configured as an eyepiece 8 (not shown in greater detail) for the operating personnel, such as the physician. This eyepiece 8 is connected with an optical image guide 25 which, like the optical light guide 23, extends inside the endoscope to the distal end thereof.

At the distal end 3 of the endoscope or the shaft 1, there is an endoscope head 27, which is sealed off from the ambience like the entire shaft 1.

Figure 5:
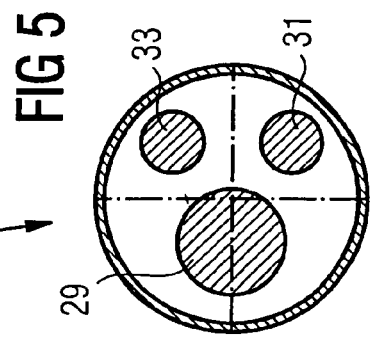
FIG. 5 shows a front view of the detail according to FIG. 4.

As will be apparent from FIG. 5, the endoscope head includes an image lens 29 which is connected with the optical image guide 25 inside the shaft, and two light lenses 31 and 33, which are connected with the optical light guide via a Y-connection in the interior of the shaft, which comprises a free space 10 (see FIG. 2) in the form of a channel, for example, in a manner which is not shown in greater detail.

As shown in FIG. 1, for reasons of stability, the leaf spring 9 is surrounded by an elastic net 35, which consists of steel braiding, for example, and which is sheathed by a flexible sleeve 37 made of plastic material or rubber. This sleeve 37 seals off the shaft 1 and, as the case may be, also the head 27 from the ambience and, advantageously, reduces friction inside a tube or catheter at the same time.

As will be apparent from FIG. 1, the ropes 11 to 11'''' and 13 to 13'''' guided in guide elements along an axis parallel to the longitudinal axis L terminate at their ends opposite to the proximal end at different distances from the proximal end. Their end points are fixedly connected with the corresponding guide elements, for example by laser welding, or they have a larger head which projects from the corresponding guide element in the distal direction and serves as a stop means to this guide element in the proximal direction.

For reasons of clarity, only the ropes 11', 11'' and 13'' as well as their ends 43, 41 and 39 are illustrated in FIG. 1. In the preferred embodiment shown in the drawing, the ropes are subdivided in pairs of approximately the same rope length, point-symmetrically or symmetrically with the axis H, for example; the pairs of ropes (such as 11; 13, 11'; 13', 11''; 13'', 11'''; 13''' and 11''''; 13'''') are fixed to the shaft 1 or the leaf spring 9 at different distances from the proximal end 5 or form a stop means in the direction towards the proximal end 5, i.e. in the pulling direction of the ropes.

The different fixing points may subdivide the shaft into sections of equal length; in the area which is likely to be subjected to strong bending forces by specific forms of use of the device, the distances may advantageously be chosen to be smaller in order to define the bending action more exactly. Contrasting to this, in parts which are likely to remain straight or parts in which no specific exact bending is desired, the distances may be made larger. As is apparent from FIG. 1, after clamping or fixing the rope ends, stiffening of the last shape chosen in the flexible condition will occur in the direction of fixing. Here, the rope lengths of ropes 11 to 11'''' and 13 to 13'''' are fixed, and thus also the distances of the fixing points, i.e. the respective rope ends 39, 41, 43 etc., from the distal end. Of course, the number of ropes and of fixing points may be increased in order to keep the possible extension or elongation between longitudinally adjacent fixing points within small tolerances. Furthermore, in the arrangement in pairs, stability is supported not only by the pulling force, but also by the pushing force of the respective partner of a traction rope. Moreover, the leaf spring 9, too, has a certain tendency to subdivide the entire distance between two adjacent fixing points in the longitudinal direction into equal distances of adjacent turns or adjacent guide elements 19 in the longitudinal direction in this area, if possible.

As, in the embodiment illustrated, the endoscope-type device is to be used for emergency intubation, an S-shape is to be obtained for anatomic reasons, for example, which has to be given to a flexible tube or catheter which has previously been placed onto the shaft.

This S-shape is to be formed in one plane so that lateral forces can be exerted when introducing the device, too. To achieve this, in the embodiment, the lateral guide means 15 and 17 are not only connected to the shaft 1 or the leaf spring 9 at their end points— contrasting to the guided ropes 11 to 11'''' and 13 to 13''''—, but at several, advantageously all points at which they contact the leaf spring 9 along the longitudinal axis thereof. In this way, the opposite sides are neither extendable nor compressible along these axes in their length, so bending of the shaft 1 in the plane of the two lateral guide means 15 and 17, i.e. in a plane perpendicular to the plane of the drawing FIG. 1, is avoided.

After the pharynx has been opened with one hand using a laryngoscope, the shaft 1 with the tube is introduced into the lung via the trachea with the other hand.

If the previously formed S-shape should prove to be not ideal when introducing the device, it is possible to change the stable shape by releasing the fixing device using the operating lever 21 so that the portion which has already partially been introduced adjusts to the different S-shape. In this shape which has been adjusted to the anatomic conditions of the individual case, the device can be further introduced until the physician detects via the eyepiece 8 that the entrance to the lung has been reached. Then, the rigid S-form of the endoscope is changed by releasing the fixing device so that the endoscope, which is now flexible, or the shaft 1 thereof can be pulled out of the tube. There are no or only very small frictional forces between the flexible tube and the shaft 1 so that inadvertent extraction of the tube is avoided.

The invention is not limited to endoscopy, particularly emergency intubation, but may be applied to all endoscope-type devices. It is pointed out explicitly that this term is to be interpreted broadly according to the invention; for example, bendable shafts in technology relating to tools, particularly for extending screw drivers, drills and the like, and bendable links which are configured to be flexible or bendable at least in partial portions and in which stiffening to an arbitrary predetermined shape is desired, are to be included in this definition. Advantageously, the formability and flexibility described above may exist along the entire shaft 1.

What is claimed is:

1. A device including:
   (a) a shaft having at least one flexible portion along its length between a proximal end and a distal end;
   (b) at least two longitudinally bendable pulling and/or pushing elements, the at least two pulling and/or pushing elements each extending to the proximal end of the shaft and each acting on the shaft in an axial direction of the shaft at locations spaced apart from the proximal end of the shaft further than at least part of the at least one flexible portion; and
   (c) a fixing device located in a fixed position with respect to the shaft adjacent to the proximal end of the shaft, the fixing device having each of the at least two pulling and/or pushing elements extending there through, and being adapted to reside alternatively in a releasing position in which the pulling and/or pushing elements are unsecured to the fixing device and are substantially free to move axially there through, or a locking position in which each pulling and/or pushing element is fixed in place with respect to the fixing device.

2. The device of claim 1 wherein the shaft comprises a leaf spring having a ring-shaped cross-section.

3. The device of claim 1 wherein each pulling and/or pushing element comprises a rope which is substantially rigid in its longitudinal direction.

4. The device of claim 1 wherein each pulling and/or pushing element is received within a respective guide element within the shaft so as to be slidable longitudinally with respect to the respective guide element.

5. The device of claim 1 wherein the pulling and/or pushing elements are mounted in the shaft at an inner circumference of the shaft.

6. The device of claim 1 wherein each pulling and/or pushing element acts upon the shaft in such a way that it is limited to pulling and pushing directions for the respective pulling and/or pushing element.

7. The device of claim 1 further including two lateral guides extending longitudinally inside the shaft on opposite sides thereof, each lateral guide being fixed to the shaft along at least a portion of the length of the respective lateral guide.

8. The device of claim 1 wherein the shaft includes an interior longitudinal channel.

9. The device of claim 8 further including an optical light guide or an optical image guide extending within the channel.

10. The device of claim 1 wherein the pulling and/or pushing elements are arranged in pairs with each pulling and/or pushing element in a respective pair engaging the shaft in the axial direction at substantially the same distance from the proximal end of the shaft.

11. The device of claim 1 wherein the pulling and/or pushing elements are arranged symmetrically about the shaft.

12. A device including:
    (a) a shaft having at least one flexible portion along its length between a proximal end and a distal end;
    (b) at least two longitudinally bendable pulling and/or pushing elements, the at least two pulling and/or pushing elements each extending to the proximal end of the shaft and each acting on the shaft in an axial direction of the shaft at locations spaced apart from the proximal end of the shaft; and
    (c) a fixing device located at or adjacent to the proximal end of the shaft, the fixing device in a releasing position leaving the pulling and/or pushing elements unsecured to the fixing device so that the pulling and/or pushing elements are substantially free to move axially through the fixing device to enable the shaft to be bent to a desired shape, and the fixing device in a locking position locking the pulling and/or pushing elements in place with respect to the fixing device to retain the shaft in the desired shape.

13. The device of claim 12 wherein the shaft comprises a leaf spring having a ring-shaped cross-section.

14. The device of claim 12 wherein each pulling and/or pushing element is received within a respective guide element within the shaft so as to be slidable longitudinally with respect to the respective guide element.

15. The device of claim 12 further including two lateral guides extending longitudinally inside the shaft on opposite sides thereof, each lateral guide being fixed to the shaft along at least a portion of the length of the respective lateral guide.

16. The device of claim 12 wherein the shaft includes an interior longitudinal channel.

17. A method for operating an endoscope-type device having a shaft with at least one flexible portion along its length between a proximal end and a distal end and at least two longitudinally bendable pulling and/or pushing elements, the at least two pulling and/or pushing elements each extending to the proximal end of the shaft and each acting on the shaft in an axial direction of shaft at locations spaced apart from the proximal end of the shaft, the method including the steps of:
    (a) placing the at least two pulling and/or pushing elements in a condition in which they are freely movable axially at the proximal end of the shaft and bending the shaft to a desired longitudinally bent shape;

(b) with the shaft in the desired bent shape, placing the at least two pulling and/or pushing elements in a condition in which they are in a fixed position prevented from moving axially at the proximal end of the shaft to fix the shaft in the desired bent shape;

(c) inserting the shaft into an inserted position in an orifice while the at least two pulling and/or pushing elements are in the fixed position fixing the shaft in the desired bent shape;

(d) with the shaft in the inserted position, placing the at least two pulling and/or pushing elements in the condition in which they are freely movable axially at the proximal end of the shaft; and (e) moving the shaft from the inserted position in the orifice while the at least two pulling and/or pushing elements are in the condition in which they are freely movable axially at the proximal end of the shaft.

18. The method of claim 17 wherein the step of moving the shaft from the inserted position in the orifice includes adjusting the position of the shaft to a different bent shape and further including the steps of:

(a) again placing the at least two pulling and/or pushing elements in the condition in which they are prevented from moving axially at the proximal end of the shaft to fix the shaft in the different bent shape;

(b) adjusting the position of the shaft in the orifice to an adjusted position;

(c) again placing the at least two pulling and/or pushing elements in the condition in which they arc freely movable axially at the proximal end of the shaft; and (d) entirely withdrawing the shaft from the orifice while the at least two pulling and/or pushing elements are in the condition in which they are freely movable axially at the proximal end of the shaft.

* * * * *

UNITED STATES PATENT AND TRADEMARK OFFICE
CERTIFICATE OF CORRECTION

PATENT NO. : 6,887,195 B1
DATED : May 3, 2005
INVENTOR(S) : Tonis Pilvisto

It is certified that error appears in the above-identified patent and that said Letters Patent is hereby corrected as shown below:

Column 10,
Line 11, change "arc" to -- are --.

Signed and Sealed this

Fifth Day of July, 2005

JON W. DUDAS
*Director of the United States Patent and Trademark Office*